(12) United States Patent
Hatlestad et al.

(10) Patent No.: US 8,905,938 B2
(45) Date of Patent: Dec. 9, 2014

(54) BIO-IMPEDANCE SENSOR AND SENSING METHOD

(75) Inventors: John D. Hatlestad, Maplewood, MN (US); Marina Brockway, Shoreview, MN (US); Yousufali Husaini Dalal, Northridge, CA (US); Loell Boyce Moon, Ham Lake, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 93 days.

(21) Appl. No.: 13/479,967

(22) Filed: May 24, 2012

(65) Prior Publication Data

US 2012/0245475 A1    Sep. 27, 2012

Related U.S. Application Data (63) Continuation of application No. 11/312,278, filed on Dec. 20, 2005, now Pat. No. 8,204,585.

(51) Int. Cl.
| | | |
|---|---|---|
| A61B 5/08 | (2006.01) | |
| A61N 1/365 | (2006.01) | |
| A61B 5/00 | (2006.01) | |
| A61B 5/053 | (2006.01) | |
| A61N 1/39 | (2006.01) | |
| A61N 1/368 | (2006.01) | |

(52) U.S. Cl.
CPC ............ *A61B 5/0535* (2013.01); *A61N 1/3962* (2013.01); *A61N 1/3684* (2013.01); *A61N 1/36521* (2013.01); *A61B 5/7207* (2013.01); *A61B 5/0809* (2013.01)
USPC .......................................... 600/484; 600/547

(58) Field of Classification Search
USPC ....................................................... 600/484
See application file for complete search history.

(56) References Cited

U.S. PATENT DOCUMENTS

| 4,928,688 | A | 5/1990 | Mower |
|---|---|---|---|
| 5,334,222 | A | 8/1994 | Salo et al. |
| 6,026,320 | A | 2/2000 | Carlson et al. |
| 6,221,011 | B1 | 4/2001 | Bardy |
| 6,270,457 | B1 | 8/2001 | Bardy |
| 6,277,072 | B1 | 8/2001 | Bardy |
| 6,280,380 | B1 | 8/2001 | Bardy |
| 6,285,907 | B1 | 9/2001 | Kramer et al. |
| 6,312,378 | B1 | 11/2001 | Bardy |
| 6,336,903 | B1 | 1/2002 | Bardy |
| 6,358,203 | B2 | 3/2002 | Bardy |
| 6,368,284 | B1 | 4/2002 | Bardy |
| 6,371,922 | B1 | 4/2002 | Baumann et al. |
| 6,398,728 | B1 | 6/2002 | Bardy |
| 6,411,848 | B2 | 6/2002 | Kramer et al. |

(Continued)

OTHER PUBLICATIONS

File History for U.S. Appl. No. 11/312,278, 283 pages.

*Primary Examiner* — Max Hindenburg
*Assistant Examiner* — Renee Danega
(74) *Attorney, Agent, or Firm* — Seager, Tufte & Wickhem, LLC (57) ABSTRACT

Implantable medical devices and techniques are implemented that use bio-impedance to measure aspects of patient physiology. A signal separation method is performed at least in part in an implantable device. The method involves detecting a plurality of impedance signals using a plurality of implantable electrodes coupled to the implantable device. The method further involves separating one or more signals from the plurality of impedance signals using a signal separation technique, such as an algorithm-based separation technique.

9 Claims, 7 Drawing Sheets

(56) References Cited

U.S. PATENT DOCUMENTS

| | | |
|---|---|---|
| 6,424,865 B1 | 7/2002 | Ding |
| 6,440,066 B1 | 8/2002 | Bardy |
| 6,459,929 B1 | 10/2002 | Hopper et al. |
| 6,463,326 B1 | 10/2002 | Hartley et al. |
| 6,480,733 B1 | 11/2002 | Turcott |
| 6,542,775 B2 | 4/2003 | Ding et al. |
| 6,597,951 B2 | 7/2003 | Kramer et al. |
| 6,684,101 B2 * | 1/2004 | Daum .................. 600/547 |
| 7,236,819 B2 | 6/2007 | Brockway et al. |
| 7,260,432 B2 | 8/2007 | Kramer et al. |
| 7,555,335 B2 | 6/2009 | Kamath et al. |
| 7,653,436 B2 | 1/2010 | Schecter |
| 7,706,866 B2 | 4/2010 | Zhang et al. |
| 2002/0002389 A1 | 1/2002 | Bradley et al. |
| 2003/0130702 A1 | 7/2003 | Kramer et al. |
| 2004/0102712 A1 | 5/2004 | Belalcazar et al. |
| 2004/0116819 A1 | 6/2004 | Alt |
| 2004/0230128 A1 | 11/2004 | Brockway et al. |
| 2004/0230243 A1 * | 11/2004 | Haefner et al. .................. 607/27 |
| 2005/0061320 A1 | 3/2005 | Lee et al. |
| 2005/0119586 A1 | 6/2005 | Coyle et al. |
| 2005/0288600 A1 | 12/2005 | Zhang et al. |
| 2006/0241512 A1 * | 10/2006 | Kwok et al. .................. 600/547 |
| 2007/0142733 A1 | 6/2007 | Hatlestad et al. |

* cited by examiner

BIO-IMPEDANCE SENSOR AND SENSING METHOD

RELATED APPLICATIONS

This application is a continuation of U.S. patent application Ser. No. 11/312,278, filed on Dec. 20, 2005, which is hereby incorporated herein by reference.

FIELD OF THE INVENTION

The present invention relates generally to implantable medical devices and, more particularly, to implanted devices and techniques that use bio-impedance to measure aspects of patient physiology.

BACKGROUND OF THE INVENTION

Heart failure is an abnormality of cardiac function that causes cardiac output to fall below a level adequate to meet the metabolic demand of peripheral tissues. Heart failure is often referred to as congestive heart failure (CHF) due to the accompanying venous and pulmonary congestion. Heart failure may have a variety of underlying causes, including ischemic heart disease (coronary artery disease), hypertension (high blood pressure), and diabetes, among others. It has been observed that respiratory disruption can be particularly serious for patients concurrently suffering from cardiovascular deficiencies, such as heart failure. Unfortunately, disordered breathing is often undiagnosed. If left untreated, the effects of disordered breathing may result in serious health consequences for the patient.

Because of the need for early evaluation of heart failure and/or disordered breathing symptoms, an effective approach to monitoring and early diagnosis is desired. Acquiring accurate physiological sensor information may allow for early intervention, preventing serious heart failure decompensation and hospitalization.

SUMMARY OF THE INVENTION

The present invention is directed to implantable medical devices and techniques that use bio-impedance to measure aspects of patient physiology. In accordance with an embodiment of the present invention, a signal separation method is performed at least in part in an implantable device. The method involves detecting a plurality of impedance signals using a plurality of implantable electrodes coupled to the implantable device. The method further involves separating one or more signals according to their sources from the plurality of impedance signals using a signal separation technique, such as an algorithm-based separation technique.

Methods of the present invention may involve storing the separated signal(s) within the implantable device. Methods may involve using the separated one or more signals within the implantable device for a variety of purposes. The separated signal(s) from the implantable device may be transmitted to a patient-external location or device, such as a portable or bed-side communications device or an interface device of a networked patient management system.

Various signal separation techniques may be implemented. For example, one suitable signal separation technique involves forming a linear combination of impedance signals that increases a signal-to-noise ratio for the separated one or more signals. Forming the linear combination may involve forming the linear combination of impedance signals using blind source separation. Another suitable signal separation technique involves an adaptive noise cancellation technique.

Methods of the present invention may further involve identifying the one or more separated signals with one or more signals of interest. One approach involves identifying one or more separated signals by the maximum of the correlation between the separated signal(s) and the signal of interest. The one or more signals of interest may comprise a physiological signal. For example, the physiological signal of interest may be a signal associated with respiration or cardiac activity. The physiological signal may be a signal useful for detecting presence of thoracic fluid.

Identifying the one or more separated signals may involve matching a morphology of a separated signal with a morphology of a signal of interest. For example, identifying the one or more separated signals may involve matching frequency content of a separated signal with frequency content of a signal of interest. Identifying the one or more separated signals may involve matching timing of events within a separated signal with timing of events within a signal of interest.

In accordance with another embodiment, an implantable medical device may be configured to include a plurality of implantable electrodes each configured for sensing an impedance signal, thereby providing a plurality of impedance signals. The implantable medical device may include a processor coupled to the plurality of electrodes and configured to receive the plurality of impedance signals. The processor may further be configured to separate one or more signals from the plurality of impedance signals using a signal separation technique.

The processor is typically coupled to memory, and the separated one or more signals may be stored in the memory. The device preferably includes communication circuitry coupled to the processor. The communication circuitry may be configured to transfer the separated one or more signals to a patient-external receiver. The patient-external receiver may be part of a patient-worn or held communications device, a bed-side device, or a communications interface of a networked patient management system.

The processor may be configured to form a linear combination of impedance signals that increases a signal-to-noise ratio for the separated one or more signals. For example, the processor may be configured to perform blind source separation when forming the linear combination of impedance signals. Alternatively, the processor may be configured to perform adaptive noise cancellation to separate the one or more signals.

The processor may be configured to identify the one or more separated signals with one or more signals of interest, such as a physiological signal. Physiological signals of interest may include a signal associated with one or more of respiration, cardiac activity, and a signal useful for detecting presence of thoracic fluid.

The processor may be configured to perform matching of a morphology of a separated signal with a morphology of a signal of interest. The processor may be configured to perform matching of frequency content of a separated signal with frequency content of a signal of interest. The processor may be configured to perform matching of timing of events within a separated signal with timing of events within a signal of interest.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings, which form a part hereof, and in which is shown by way of illustration, various embodiments in which the invention may be practiced. It is to be understood that other embodiments may be utilized, and structural and functional changes may be made without departing from the scope of the present invention.

An implanted device according to the present invention may include one or more of the features, structures, methods, or combinations thereof described hereinbelow. For example, a cardiac monitor or a cardiac stimulator may be implemented to include one or more of the advantageous features and/or processes described below. It is intended that such a monitor, stimulator, or other implanted or partially implanted device need not include all of the features described herein, but may be implemented to include selected features that provide for unique structures and/or functionality. Such a device may be implemented to provide a variety of therapeutic or diagnostic functions.

Devices implemented in accordance with the present invention are generally referred to herein as a patient implantable medical device (PIMD), which may include a housing implanted under the skin in the chest region of a patient. A PIMD may, for example, be implanted subcutaneously such that all or selected elements of the device are positioned on the patient's front, back, side, or other body locations suitable for sensing cardiac activity and delivering cardiac stimulation therapy. It is understood that elements of the PIMD may be located at several different body locations, such as in the chest, abdominal, or subclavian region, with electrode elements respectively positioned at different regions near, around, in, or on the heart. For example, a PIMD may include one or more of endocardial leads, epicardial leads, subcutaneous leads, sensor or electrode modules and arrays, and/or other leads or sensors.

PIMDs, such as cardiac rhythm management devices, of the present invention preferably employ lead electrode configurations that are configured to measure bio-impedance across multiple vectors, including a variety of intracardiac, trans-cardiac, and trans-thoracic vectors. Impedance measurements across any of these vectors are typically influenced by multiple aspects of patient physiology, including respiratory and cardiac activity. PIMDs and sensing techniques according to embodiments of the present invention advantageously provide for separating out the effects of these individual physiological source signals from the impedance measurement by using multiple impedance measurement vectors.

PIMDs and sensing techniques according to embodiments of the present invention advantageously provide an optimal linear combination of a multiplicity of impedance vectors to enable higher sensitivity of the combined signal to a physiologic parameter of interest. Such physiologic parameters of interest may include lung fluid, respiratory components, or cardiac components. By including a local impedance in the linear combination, the combined signal could be made robust to physiologic noises, such as hematocrit or electrolyte changes, for example. By way of further example, intra-cardiac impedance signals may be useful for patient hemodynamic monitoring and assessment. Cardiac output and volume may be assessed, as can be filling and/or ejection patterns particularly useful for optimizing cardiac resynchronization therapy. PIMDs and sensing techniques may provide for higher specificity and sensitivity for an advanced generation bio-impedance sensor.

Some implanted devices use transthoracic impedance to monitor minute ventilation. A typical technique involves filtering out the portion of the impedance signal caused by the cardiac contraction or "stroke." This approach can be successful if the heartbeat frequency is consistently higher than the frequency of respiration. This conventional approach has been used successfully for years to measure minute ventilation for rate responsive pacing.

Recently, research into using this same respiration sensing technology to provide diagnostic measures of respiration in heart failure patients has identified limitations in such conventional approaches. In certain situations, for example, the heart rate may not always be consistently higher than the respiratory rate. In other situations, heart rate may be too unstable (e.g., atrial fibrillation) to effectively remove the cardiac stroke component.

In these cases, the cardiac stroke component cannot be effectively filtered out without also affecting the respiratory signal that one is attempting to measure. It has been observed that traditional signal processing techniques based on measurements along a single impedance vector are not always successful in removing cardiac stroke components from transthoracic impedance waveforms. These limitations may not significantly affect the performance of rate responsive pacing, but have been shown to lead to highly erroneous diagnostic measures of respiration. The present inability to successfully remove or significantly attenuate the cardiac stroke component under varied physiologic conditions can lead to falsely elevated estimates of respiration. Moreover, patient hemodynamic monitoring using single-vector impedance measurements have not proven successful.

PIMDs and sensing techniques according to the present invention are implemented to overcome the limitations of conventional approaches such as, for example, by attenuating the cardiac stroke component of an impedance signal to improve the accuracy of respiration sensing. According to embodiments of the invention, known signal processing algorithms employed for adaptive noise cancellation in communications channels (e.g., echo cancellation in telephone systems) may be advantageously exploited and adapted for use in the context of the present invention. An adaptive noise cancellation approach of the present invention removes components correlated to a measured noise source from a composite signal (i.e., signal of interest plus noise).

In other embodiments, an algorithm may be employed to separate signal components originating from different sources, e.g., separating cardiac stroke and respiratory signals from low signal-to-noise (SNR) ratio signals using a separation technique, such as blind source separation. According to one approach, a PIMD is configured to identify an optimal combination of the impedance vector signals that makes cardiac and respiration components, as well as noise, independent (i.e., orthogonal) to one another. This technique relies upon the principle that signals arising from a common source, when sensed by spatially distributed electrodes, will be correlated strongly in time and in space along a particular direction.

According to an embodiment that employs a source separation approach, respiratory and cardiac components can be isolated by revealing the correlated spatial components with a time-averaged cross-correlation matrix. Such an approach further includes projecting signals on an orthonormal basis, which makes the components from the different sources orthogonal (i.e., uncorrelated) to one another. A separation technique such as blind source separation, for example, uses statistical signal processing to enhance spatial correlation and find these optimal directions (i.e., linear combination coefficients).

It is known that respiratory disturbances are a hallmark of heart failure decompensation. Respiratory diagnostics can play a central role in decompensation prediction and detection, particularly in the context of an advanced patient management system as described herein. Respiration sensing, however, must be sufficiently accurate to enable reliable respiratory diagnostic trending. Cardiac stroke components leaking into the respiratory waveform, for example, have been demonstrated to corrupt respiratory diagnostic measures.

Devices and methods implemented in accordance with the present invention enable more reliable respiration sensing, even in cases of unstable heart rate, and in cases of overlapping heart and respiratory rates. Devices and methods of the present invention can be implemented to provide useful hemodynamic measures via joint processing of multiple cardiac impedance vectors. Devices and methods can be implemented to provide for closed loop cardiac resynchronization therapy optimization by use of cardiac impedance parameters in accordance with the present invention.

Although aspects of the present invention focus on removing cardiac stroke from transthoracic impedance, it is understood that the present invention has applicability to the more general problem of separating multiple physiological signals from impedance measurements along multiple vectors.

Sensing and/or stimulation devices that separate individual impedance signals from multiple sensed impedance signals in accordance with the present invention may be adapted to their implant environment manually, such as by a clinician after implantation, or may be adapted to automatically configure themselves. Electrode arrays and/or multiple electrodes provide for many possible combinations useful for sensing impedance, respiratory activity, cardiac activity, patient activity, and other signals useful for evaluating patient well-being and treating adverse patient conditions, such as cardiac arrhythmia.

Turning now to the figures, FIGS. 1-4 illustrate various methodologies directed to separating one or more signals from a multiplicity of impedance signals using a algorithmic signal separation technique. In general terms, embodiments of the present invention are directed to the use of impedance from various vectors to separate out various sources. For example, devices and methods of the present invention preferably involve jointly or concurrently processing impedance signals from multiple vectors for a wide variety of purposes. Useful vectors include intracardiac, trans-cardiac, and transthoracic vectors.

Figure 1:
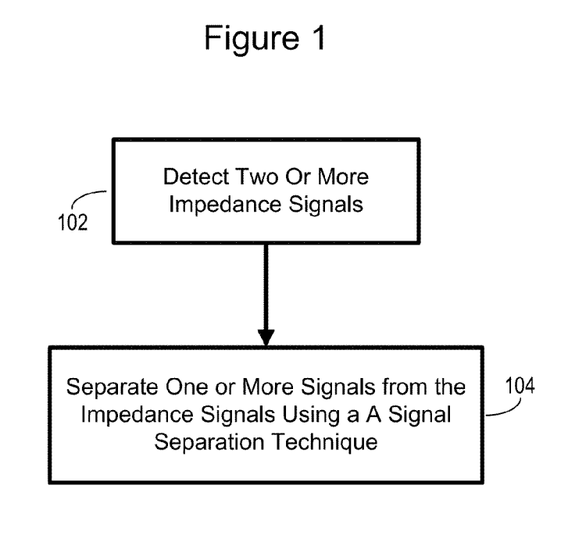
FIG. 1 is a flow diagram of a method useful for separating one or more signals of interest from a multiplicity of impedance signals in accordance with an embodiment of the present invention.

FIG. 1 is a flow diagram of a method useful for separating one or more signals of interest from a multiplicity of impedance signals in accordance with an embodiment of the present invention. According to FIG. 1, two or more impedance signals are detected 102, typically using a multiplicity of implantable electrodes. One or more signals are separated 104 from the detected impedance signals using an algorithmic separation technique. According to one approach, signal separation 104 may involve an adaptive noise cancellation technique. According to another approach, signal separation may involve a source separation technique, such as blind source separation.

Figure 2:
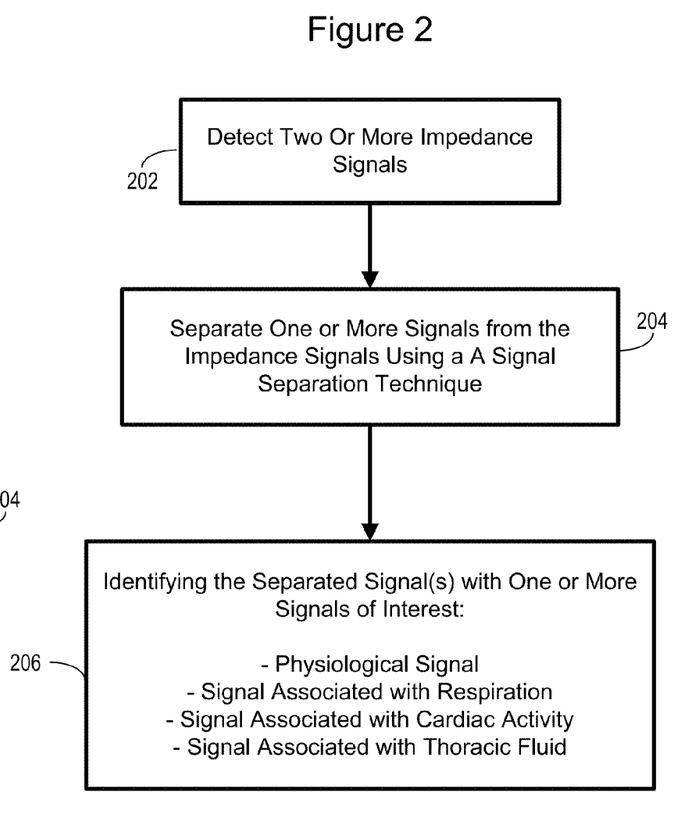
FIG. 2 is a flow diagram of a method useful for separating one or more signals of interest from a multiplicity of impedance signals in accordance with another embodiment of the present invention.

FIG. 2 is a flow diagram of a method useful for separating one or more signals of interest from a multiplicity of impedance signals in accordance with another embodiment of the present invention. According to FIG. 2, two or more impedance signals are detected 202, and one or more signals are separated 204 from the detected impedance signals using an algorithmic separation technique. The method of FIG. 2 further involves identifying 206 the separated signal(s) with one or more signals of interest. One approach involves identifying one or more separated signals by the maximum of the correlation between the separated signal(s) and the signal of interest. A physiological signal represents one such signal of particular interest. The signal of interest may be a signal associated with respiration, a signal associated with cardiac activity, or a signal associated with thoracic fluid, for example.

Figure 3:
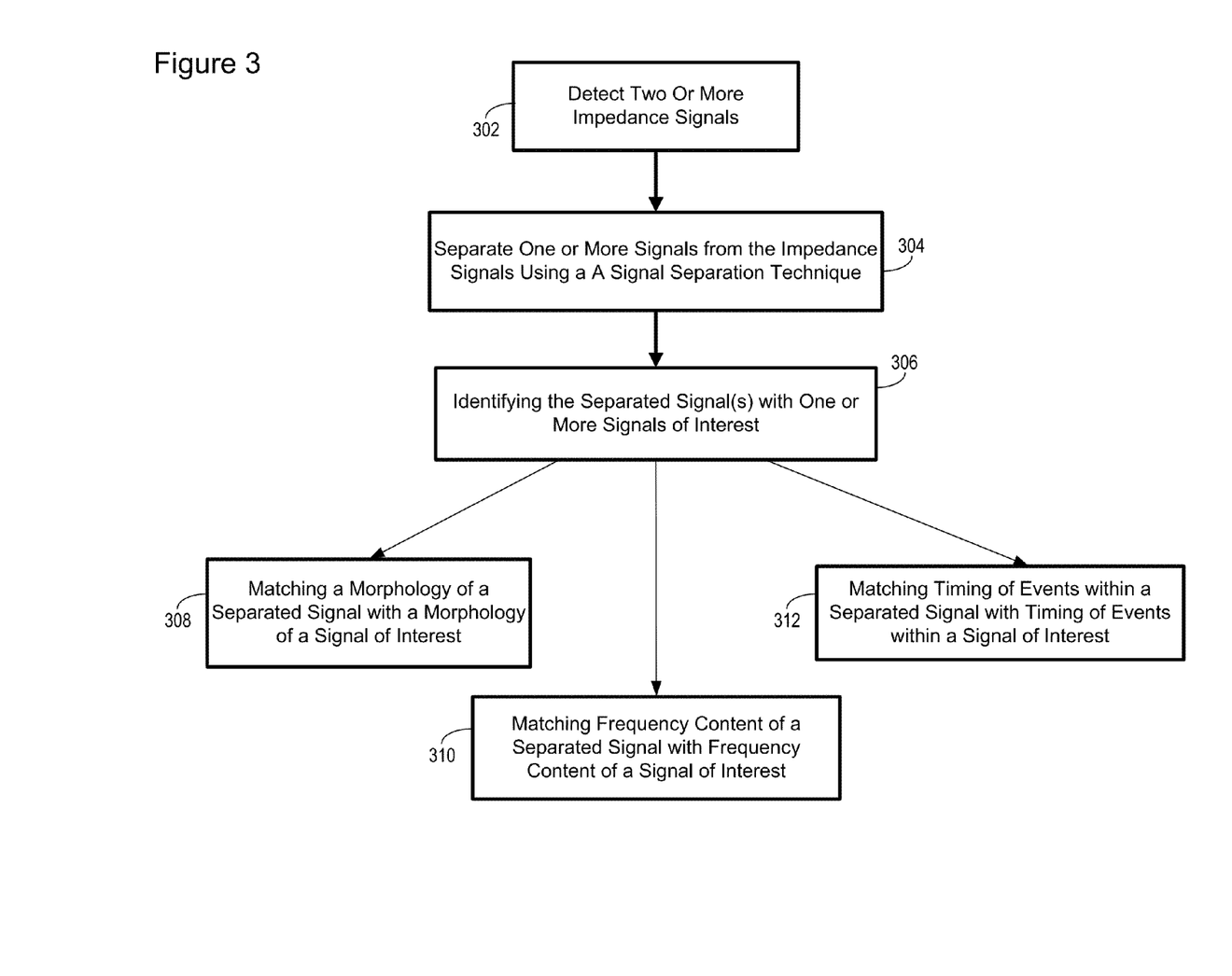
FIG. 3 is a flow diagram of a method useful for separating one or more signals of interest from a multiplicity of impedance signals in accordance with a further embodiment of the present invention.

FIG. 3 is a flow diagram of a method useful for separating one or more signals of interest from a multiplicity of impedance signals in accordance with a further embodiment of the present invention. According to FIG. 3, two or more impedance signals are detected 302, one or more signals are separated 304 from the detected impedance signals using an algorithmic separation technique, and one or more of the separated signals are identified 306 with one or more signals of interest. According to FIG. 3, identifying 306 the separated signal(s) with one or more signals of interest may involve matching 308 a morphology of a separated signal with a morphology of a signal of interest.

Morphology matching may involve comparison of morphological features, such as fiducial points, inflection points, minima, maxima, or other features, for example, and may involve computing a correlation coefficient on a feature-by-feature basis, for example. Pattern recognition and pattern matching techniques may also be used to perform the morphology matching.

For example, various known pattern and/or feature recognition techniques may be employed, such as by using neural networks and other statistical pattern recognition techniques. Such techniques may include principal component analysis, fisher and variance weight calculations and feature selection. Neural network methods may include a back propagation neural network and/or radial basis function neural network. Statistical pattern recognition may include linear discriminant analysis, quadratic discriminant analysis, regularized discriminant analysis, soft independent modeling of class analogy, and/or discriminant analysis with shrunken covariance.

Identifying 306 the separated signal(s) with one or more signals of interest may involve matching 310 the frequency content of a separated signal with the frequency content of a signal of interest. Various known frequency content matching techniques may be used, including spectral analysis techniques. For example, spectral analysis techniques may involve comparing the dominant frequency or frequencies of the signal with the frequency regions of sources of interest, or may involve comparing the morphology of the frequency content to the frequency content of a signal of interest.

Identifying 306 the separated signal(s) with one or more signals of interest may involve matching 312 timing of events within a separated signal with the timing of events within a signal of interest. Such techniques may include comparing the timings of minima and/or maxima (or other signal feature) in the signal to expected timings of sources of interest. For example, in the case of cardiac sources, the source-of-interest timings may be cardiac intervals, whereas in the case of respiratory sources, the source-of-interest timings may be respiratory intervals.

Figure 4:
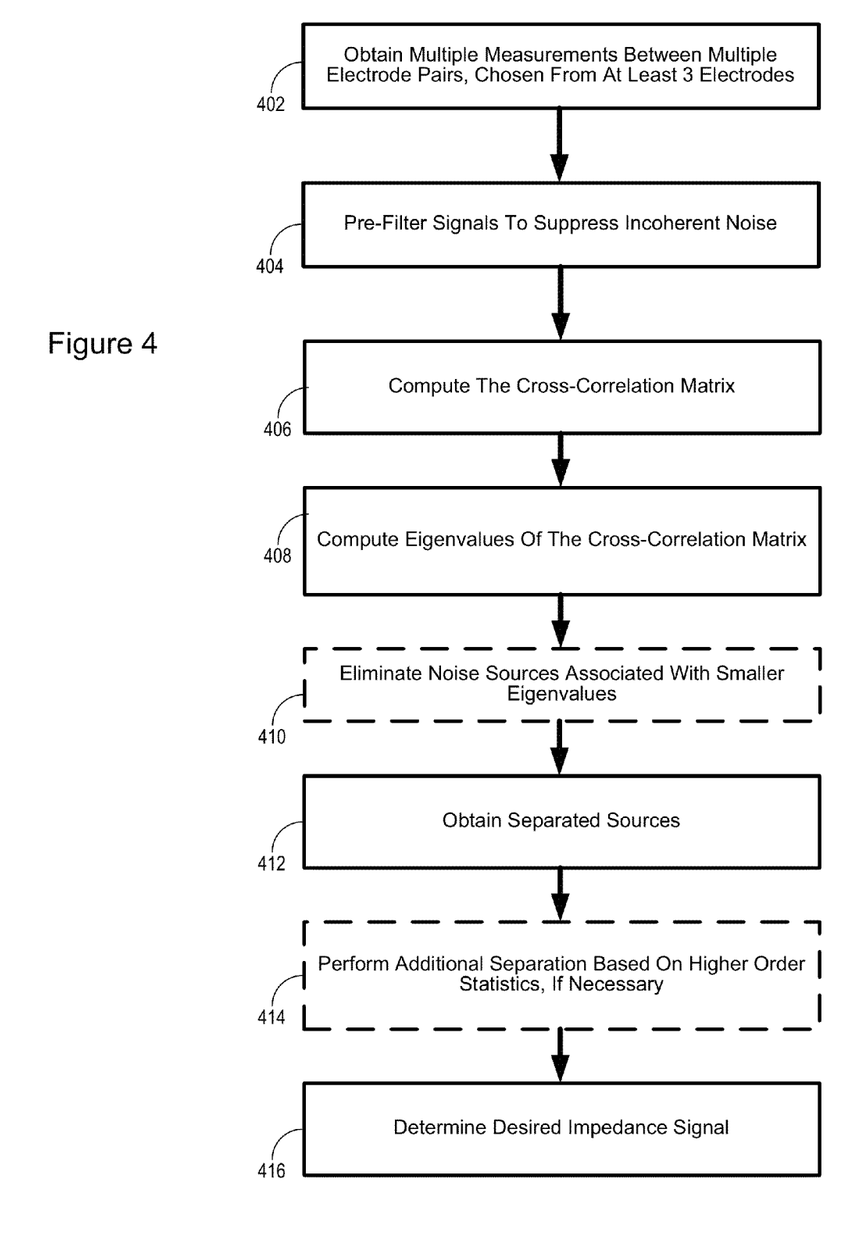
FIG. 4 is a flow diagram of a method useful for separating one or more signals of interest from a multiplicity of impedance signals in accordance with another further embodiment of the present invention.

FIG. 4 is a flow diagram of a source separation method useful for separating one or more signals of interest from a multiplicity of impedance signals in accordance with another embodiment of the present invention. The method shown in FIG. 4 involves obtaining 402 multiple concurrent measurements between multiple respective electrode pairs, chosen from at least three electrodes, for example. Collected signals may be pre-filtered 404 by, for example, a linear-phase filter to suppress broadly incoherent noise, and to generally maximize the signal-to-noise ratio.

A cross-correlation matrix may be computed 406, which may be averaged over a relatively short time interval, such as about 1 second. Eigenvalues of the cross-correlation matrix may be computed 408. The smaller eigenvalues, normally associated with noise, may be eliminated 410, by removing the noise components of the composite signals associated with those eigenvalues.

Individual signals may be separated from the composite signals using the eigenvalues. Separated sources may be obtained 412 by taking linear combinations of the recorded signals, as specified in the eigenvectors corresponding to the larger eigenvalues. Optionally, additional separation may be performed 414 based on higher order statistics, if the desired signal is not found among the signals separated at block 412.

The impedance signal may be identified 416 based on selection criteria, along with its associated vector, among the separated signals. Typically, the signal may be found among the signals associated with the largest eigenvalues. The vector associated with the selected signal may then be used to determine an impedance signal in accordance with the present invention.

The methodology illustrated in FIG. 4, such as a blind source separation technique, can use information from multiple leads to successfully restore a signal of interest even during a time when the signal is corrupted by noise or signals of other sources. In many cases, it is unlikely that any degree of filtering or signal processing based on only one lead would be able to correctly restore the signal of interest in the presence of corrupting noise. Only with the additional spatial information provided by multiple sources can the signal of interest be separated out successfully. For example, only with multiple impedance vectors can one expect to be able to separate out multiple sources of impedance fluctuations that overlap in both time and frequency.

Signal separation methodologies and electrode and vector selection methodologies useful in the context of a source separation approach of the present invention are further described in commonly owned U.S. Pat. Nos. 7,236,819 and 7,706,866, which are hereby incorporated herein by reference.

Figure 5:
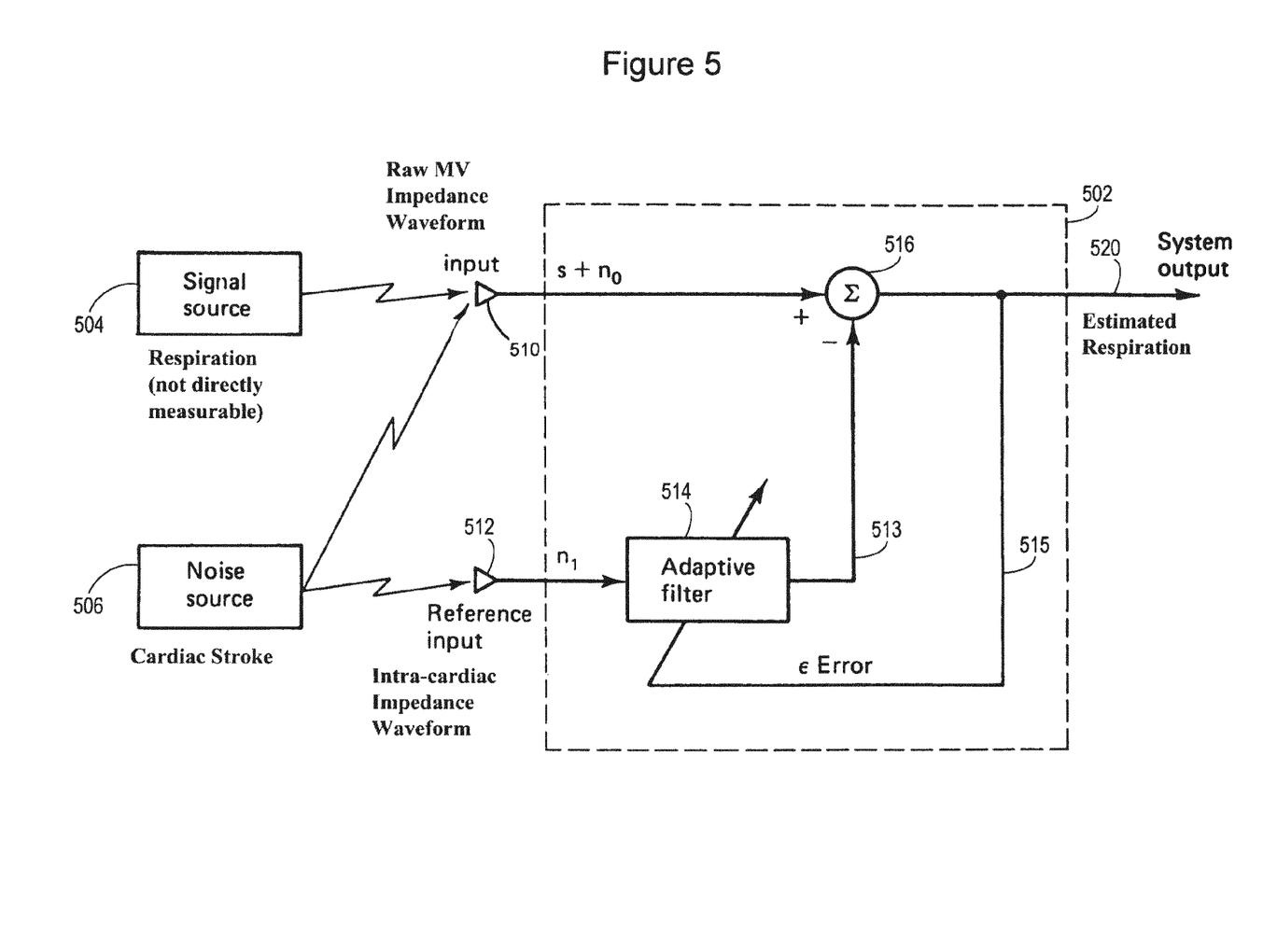
FIG. 5 is a block diagram of circuitry configured to separate one or more signals of interest from a multiplicity of impedance signals in accordance with an embodiment of the present invention.

FIG. 5 is a block diagram of circuitry configured to separate one or more signals of interest from a multiplicity of impedance signals in accordance with another embodiment of the present invention. The circuitry shown in FIG. 5 includes adaptive noise cancellation circuitry 502 that has a primary input 510 and a reference input 512. A signal source 504 is shown providing an input signal to the primary input 510. The primary input 510 is coupled to a summer 516, and presents a signal, $s+n_0$ (a composite signal comprising a signal component and a noise component), to the summer 516.

A noise source 506 is shown providing an input signal to the reference input 512. The reference input 512 is coupled to an adaptive filter 514, the output 513 of which is coupled to the summer 516. An error correction signal is communicated from the output of the summer 516 to the adaptive filter via a feedback path 515. An output signal of the noise cancellation circuitry 502 is provided at an output 520. A PIMD of the present invention may incorporate the noise cancellation circuitry shown in FIG. 5 to separate one or more signals of interest from a multiplicity of impedance signals.

In accordance with one application involving the use of the circuitry shown in FIG. 5, the signal source 504 may represent the purely respiratory portion of an impedance waveform. It is noted that this pure respiratory signal is not directly measurable in the physical system, and is, in fact, the signal of interest to be estimated from the available inputs (e.g., the primary and reference inputs 510, 512 in FIG. 5).

The noise source 506 represents the cardiac stroke component of the impedance waveforms. A replica of the cardiac stroke component can be measured in the physical system by performing an intracardiac impedance measurement. This measurement provides the signal to the reference input 512 in FIG. 5. The intracardiac impedance waveform is assumed to be a replica of the cardiac stroke component that corrupts the transthoracic impedance measurement of respiration.

In operation, the adaptive filter 514 self-adjusts its parameters to minimize the difference between the primary input signal (e.g., original raw minute ventilation impedance waveform) and the filter output 513, thereby subtracting off or effectively canceling all portions of the primary input signal that are linearly related to the cardiac stroke signal.

Figure 6:
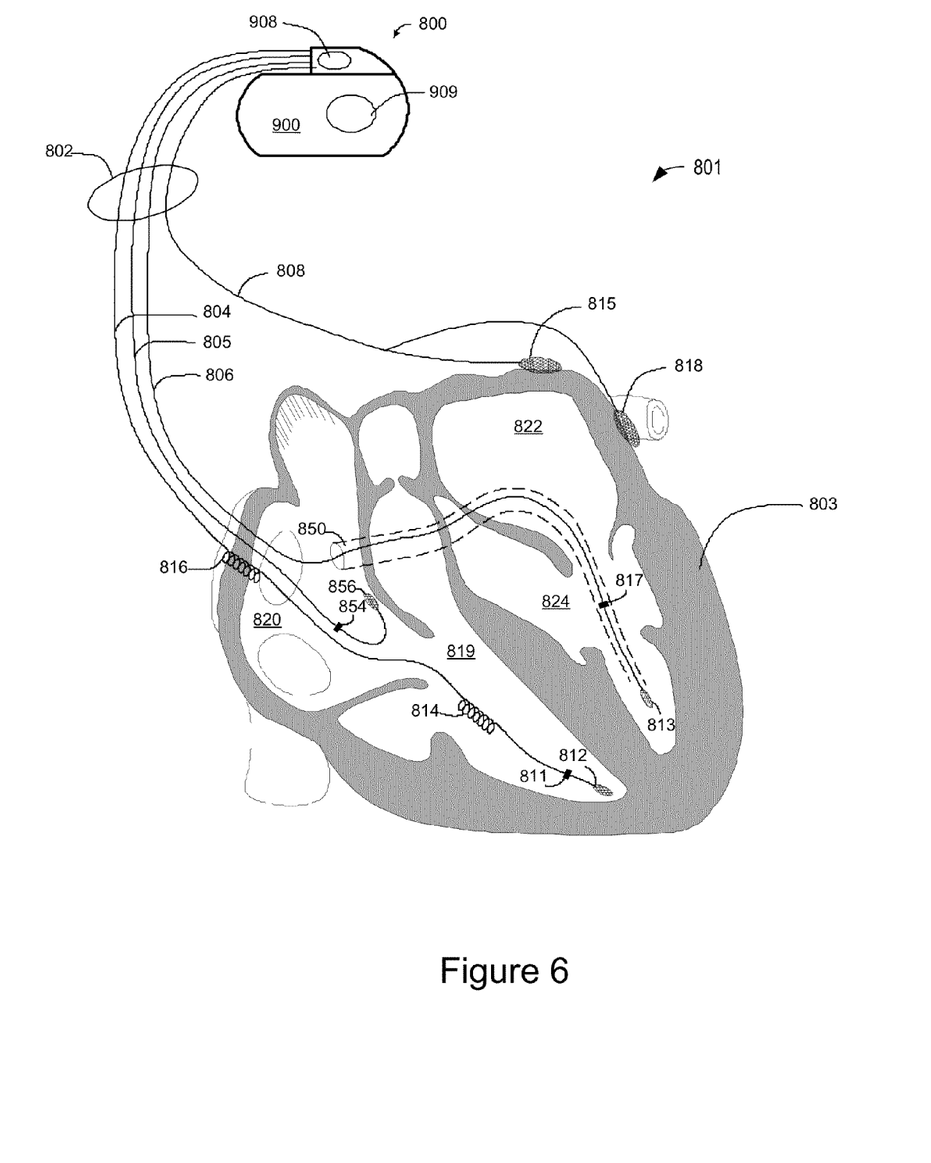
FIG. 6 shows an implantable system suitable for implementing a signal separation methodology in accordance with an embodiment of the present invention.

Turning now to FIG. 6, an implantable system in accordance with an embodiment of the present invention is shown having a lead system deployed within a heart. System 801 includes a PIMD 800 with a lead system 802 that is designed for implantation to facilitate cardiac resynchronization therapy. The lead system 802 is coupled to a detection/energy delivery system 900, which detects cardiac activity and delivers appropriate therapy via the lead system 802.

The detector/energy delivery system 900 typically includes a power supply and programmable circuit (e.g., microprocessor) coupled to an analog to digital (A-D) converter. Various lead system devices, such as electrodes and pressure sensors, can interface to the A-D converter for sensing/data collection. Alternatively, analog conditioning (e.g., filtering) may be applied to sensor signals before interfacing with the A-D converter. The detector/energy delivery system 900 also utilizes an energy delivery system. The energy delivery system may include charge capacitors and signal conditioning circuitry known in the art. The energy delivery system may interface to the programmable circuit through a D-A converter. Components and functionality of the detector/energy delivery system 900 will be further described below with reference to FIG. 7.

Still referring to FIG. 6, the PIMD system 801 is shown having the PIMD 800 electrically and physically coupled to the lead system 802. The housing and/or header of the PIMD 800 may incorporate one or more electrodes 908, 909 used to provide electrical stimulation energy to the heart and to sense cardiac electrical activity. The PIMD 800 may utilize all or a portion of the PIMD housing as a can electrode 909. The PIMD 800 may include an indifferent electrode 908 positioned, for example, on the header or the housing of the PIMD 800. If the PIMD 800 includes both a can electrode 909 and an indifferent electrode 908, the electrodes 908, 909 typically are electrically isolated from each other.

The lead system 802 is used to provide pacing signals to the heart 803, detect electric cardiac signals produced by the heart 803, and deliver electrical energy to the heart 803 under certain predetermined conditions, such as to improve cardiac output and/or to treat cardiac arrhythmias. The lead system 802 may include one or more electrodes used for pacing, sensing, and/or defibrillation. In the embodiment shown in FIG. 6, the lead system 802 includes an intracardiac right ventricular (RV) lead system 804, an intracardiac right atrial (RA) lead system 805, an intracardiac left ventricular (LV) lead system 806, and an extracardiac left atrial (LA) lead system 808. The lead system 802 of FIG. 6 illustrates one of many possible PIMD configurations. It is understood that more or fewer leads and/or electrodes of varying type may be used.

The right ventricular lead system 804 illustrated in FIG. 6 includes an SVC-coil 816, an RV-coil 814, an RV-ring electrode 811, and an RV-tip electrode 812. The right ventricular lead system 804 extends through the right atrium 820 and into the right ventricle 819. In particular, the RV-tip electrode 812, RV-ring electrode 811, and RV-coil electrode 814 are positioned at appropriate locations within the right ventricle 819 for sensing and delivering electrical stimulation pulses to the heart. The SVC-coil 816 is positioned at an appropriate location within the right atrium chamber 820 of the heart 803 or a major vein leading to the right atrial chamber 820 of the heart 803.

In one configuration, the RV-tip electrode 812 referenced to the can electrode 909 may be used to implement unipolar pacing and/or sensing in the right ventricle 819. Bipolar pacing and/or sensing in the right ventricle may be implemented using the RV-tip 812 and RV-ring 811 electrodes. In yet another configuration, the RV-ring 811 electrode may optionally be omitted, and bipolar pacing and/or sensing may be accomplished using the RV-tip electrode 812 and the RV-coil 814, for example. The right ventricular lead system 804 may be configured as an integrated bipolar pace/shock lead. The RV-coil 814 and the SVC-coil 816 are defibrillation electrodes.

The left ventricular lead 806 includes an LV distal electrode 813 and an LV proximal electrode 817 located at appropriate locations on the surface of, or about, the left ventricle 824 for pacing and/or sensing the left ventricle 824. The left ventricular lead 806 may be guided into the right atrium 820 of the heart via the superior vena cava. From the right atrium 820, the left ventricular lead 806 may be deployed into the coronary sinus ostium, the opening of the coronary sinus 850. The lead 806 may be guided through the coronary sinus 850 to a coronary vein of the left ventricle 824. This vein is used as an access pathway for leads to reach the surfaces of the left ventricle 824 which are not directly accessible from the right side of the heart. Lead placement for the left ventricular lead 806 may be achieved via subclavian vein access and a preformed guiding catheter for insertion of the LV electrodes 813, 817 adjacent to the left ventricle.

Unipolar pacing and/or sensing in the left ventricle may be implemented, for example, using the LV distal electrode referenced to the can electrode 909. The LV distal electrode 813 and the LV proximal electrode 817 may be used together as bipolar sense and/or pace electrodes for the left ventricle. The left ventricular lead 806 and the right ventricular lead 804, in conjunction with the PIMD 800, may be used to provide cardiac resynchronization therapy such that the ventricles of the heart are paced substantially simultaneously, or in phased sequence, to provide enhanced cardiac pumping efficiency in accordance with the present invention for patients suffering from heart failure.

The right atrial lead 805 includes a RA-tip electrode 856 and an RA-ring electrode 854 positioned at appropriate locations in the right atrium 820 for sensing and pacing the right atrium 820. In one configuration, the RA-tip 856 referenced to the can electrode 909, for example, may be used to provide unipolar pacing and/or sensing in the right atrium 820. In another configuration, the RA-tip electrode 856 and the RA-ring electrode 854 may be used to provide bipolar pacing and/or sensing. The lead system 802 may include one or more extracardiac leads 808 having electrodes, e.g., epicardial electrodes or sensors 815, 818, positioned at locations outside the heart for sensing and/or pacing one or more heart chambers.

Figure 7:
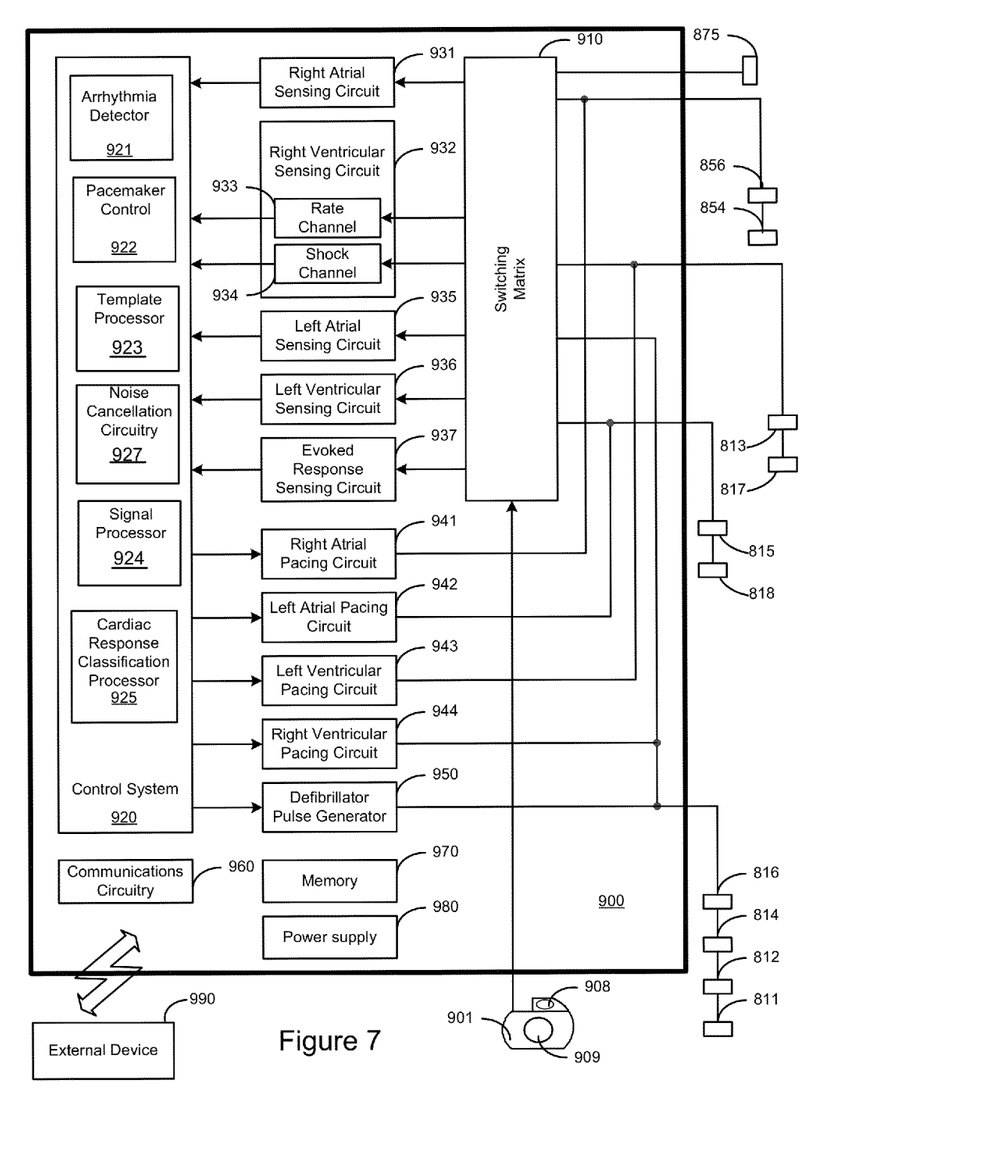
FIG. 7 shows an embodiment of an implantable medical device suitable for performing signal separation methodologies in accordance with the present invention.

Referring now to FIG. 7, there is shown an embodiment of a PIMD 900 suitable for performing signal separation methodologies in accordance with the present invention. FIG. 7 shows the PIMD 900 divided into functional blocks. It is understood by those skilled in the art that there exist many possible configurations in which these functional blocks can be arranged. The example depicted in FIG. 7 is one possible functional arrangement. Other arrangements are also possible. For example, more, fewer or different functional blocks may be used to describe a PIMD suitable for performing signal separation methodologies in accordance with the present invention. In addition, although the PIMD 900 depicted in FIG. 7 contemplates the use of a programmable microprocessor-based logic circuit, other circuit implementations may be utilized. It is also understood that the components and functionality depicted in FIG. 7 and elsewhere may be implemented in hardware, software, or a combination of hardware and software.

The PIMD 900 depicted in FIG. 7 includes circuitry for receiving cardiac signals from a heart and delivering electrical stimulation energy to the heart in the form of pacing pulses and/or defibrillation shocks. In one embodiment, the circuitry of the PIMD 900 is encased and hermetically sealed in a housing 901 suitable for implanting in a human body. Power to the PIMD 900 is supplied by an electrochemical battery 980. A connector block (not shown) is attached to the housing 901 of the PIMD 900 to allow for the physical and electrical attachment of the lead system conductors to the circuitry of the PIMD 900.

The PIMD 900 may be a programmable microprocessor-based system, including a control system 920 and a memory 970. The memory 970 may store parameters for various pacing, resynchronization, defibrillation, and sensing modes, along with other parameters. Further, the memory 970 may store data indicative of signals received by other components of the PIMD 900. The memory 970 may be used, for example, for storing historical information, impedance information, sensor information, blood flow information, perfusion information, heart sounds, heart movement, EGM information, therapy data, and/or other information, assuming appropriate sensors are provided. The historical data storage may include, for example, data obtained from long-term patient monitoring (e.g., respiratory data) used for trending patient well-being, heart failure decompensation, or other diagnostic purposes. Historical data, as well as other information, may be transmitted to an external device 990 as needed or desired. In one embodiment, the external device 990 may include a communications interface of a networked patient management system, as is discussed below.

The control system 920 and memory 970 may cooperate with other components of the PIMD 900 to control the operations of the PIMD 900. The control system depicted in FIG. 7 incorporates a processor 925 for classifying cardiac responses to pacing stimulation. The control system 920 may include additional functional components including an arrhythmia detector 921, a pacemaker control circuit 922, and a template processor 923 for cardiac signal morphology analysis, along with other components for controlling the operations of the PIMD 900.

The PIMD 900 may also include a signal processor 924 for performing signal separation in accordance with the present invention. Signal separation may be performed using the control system 920 and/or the signal processor 924 to perform the separation operations by the PIMD 900, or the signal separation may be performed in a patient-external device 990 communicatively coupled to the PIMD 900. The PIMD 900 may include noise cancellation circuitry 927 for performing signal separation in accordance with an adaptive noise cancellation methodology of the present invention. For example, the noise cancellation circuitry 927 may be configured and operate in accordance with the embodiment shown in FIG. 5.

A PIMD 900 implemented in accordance with the present invention may have a control system 920 and communications circuitry 960 that transmits its signals to a bedside signal processor when the patient is asleep. The bedside signal processor may perform a blind source separation and analysis of the signals during the patient's sleep cycle. The signal processor may then determine the appropriate impedance sensing configuration, and reprogram the PIMD before the patient awakes. The PIMD may then operate with the latest programming until the next update.

Communications circuitry 960 may be implemented to provide communications between the PIMD 900 and an external programmer unit 990 and/or APM system. In one embodiment, the communications circuitry 960 and the programmer unit 990 communicate using a wire loop antenna and a radio frequency telemetric link, as is known in the art, to receive and transmit signals and data between the programmer unit 990 and the communications circuitry 960. In this manner, programming commands and other information may be transferred to the control system 920 of the PIMD 900 from the programmer unit 990 during and after implant.

The communications circuitry 960 may also allow the PIMD to communicate with one or more receiving devices or systems situated external to the PIMD 900. By way of example, the PIMD may communicate with a patient-worn, portable or bedside communication system via the communications circuitry 960. In one configuration, one or more physiologic or non-physiologic sensors (subcutaneous, cutaneous, or external of patient) of a PIMD system may be equipped with a short-range wireless communication interface, such as an interface conforming to a known communications standard, such as Bluetooth or IEEE 802 standards. Data acquired by such sensors may be communicated to the PIMD 900 via the communications circuitry 960. It is noted that physiologic or non-physiologic sensors equipped with wireless transmitters or transceivers may communicate with a receiving system external of the patient. The external sensors in communication with the PIMD 900 may be used to facilitate patient well-being assessment, heart failure decompensation trending/tracking, cardiac resynchronization therapy adjustment and optimization, and other purposes.

In the embodiment of the PIMD 900 illustrated in FIG. 7, electrodes RA-tip 856, RA-ring 854, RV-tip 812, RV-ring 811, RV-coil 814, SVC-coil 816, LV distal electrode 813, LV proximal electrode 817, LA distal electrode 818, LA proximal electrode 815, indifferent electrode 908, and can electrode 909 are coupled through a switch matrix 910 to sensing circuits 931-937.

A right atrial sensing circuit 931 serves to detect and amplify electrical signals from the right atrium of the heart. Bipolar sensing in the right atrium may be implemented, for example, by sensing voltages developed between the RA-tip 856 and the RA-ring 854. Unipolar sensing may be implemented, for example, by sensing voltages developed between the RA-tip 856 and the can electrode 909. Outputs from the right atrial sensing circuit are coupled to the control system 920.

A right ventricular sensing circuit 932 serves to detect and amplify electrical signals from the right ventricle of the heart. The right ventricular sensing circuit 932 may include, for example, a right ventricular rate channel 933 and a right ventricular shock channel 934. Right ventricular cardiac signals sensed through use of the RV-tip 812 electrode are right ventricular near-field signals and are denoted RV rate channel signals. A bipolar RV rate channel signal may be sensed as a voltage developed between the RV-tip 812 and the RV-ring 811. Alternatively, bipolar sensing in the right ventricle may be implemented using the RV-tip electrode 812 and the RV-coil 814. Unipolar rate channel sensing in the right ventricle may be implemented, for example, by sensing voltages developed between the RV-tip 812 and the can electrode 909.

Right ventricular cardiac signals sensed through use of the RV-coil electrode 814 are far-field signals, also referred to as RV morphology or RV shock channel signals. More particularly, a right ventricular shock channel signal may be detected as a voltage developed between the RV-coil 814 and the SVC-coil 816. A right ventricular shock channel signal may also be detected as a voltage developed between the RV-coil 814 and the can electrode 909. In another configuration, the can electrode 909 and the SVC-coil electrode 816 may be electrically shorted and a RV shock channel signal may be detected as the voltage developed between the RV-coil 814 and the can electrode 909/SVC-coil 816 combination.

Left atrial cardiac signals may be sensed through the use of one or more left atrial electrodes 815, 818, which may be configured as epicardial electrodes. A left atrial sensing circuit 935 serves to detect and amplify electrical signals from the left atrium of the heart. Bipolar sensing and/or pacing in the left atrium may be implemented, for example, using the LA distal electrode 818 and the LA proximal electrode 815. Unipolar sensing and/or pacing of the left atrium may be accomplished, for example, using the LA distal electrode 818 to can vector 909 or the LA proximal electrode 815 to can vector 909.

Referring still to FIG. 7, a left ventricular sensing circuit 936 serves to detect and amplify electrical signals from the left ventricle of the heart. Bipolar sensing in the left ventricle may be implemented, for example, by sensing voltages developed between the LV distal electrode 813 and the LV proximal electrode 817. Unipolar sensing may be implemented, for example, by sensing voltages developed between the LV distal electrode 813 or the LV proximal electrode 817 and the can electrode 909.

Optionally, an LV coil electrode (not shown) may be inserted into the patient's cardiac vasculature, e.g., the coronary sinus, adjacent to the left heart. Signals detected using combinations of the LV electrodes, 813, 817, LV coil electrode (not shown), and/or can electrodes 909 may be sensed and amplified by the left ventricular sensing circuitry 936. The output of the left ventricular sensing circuit 936 is coupled to the control system 920.

Figure 8:
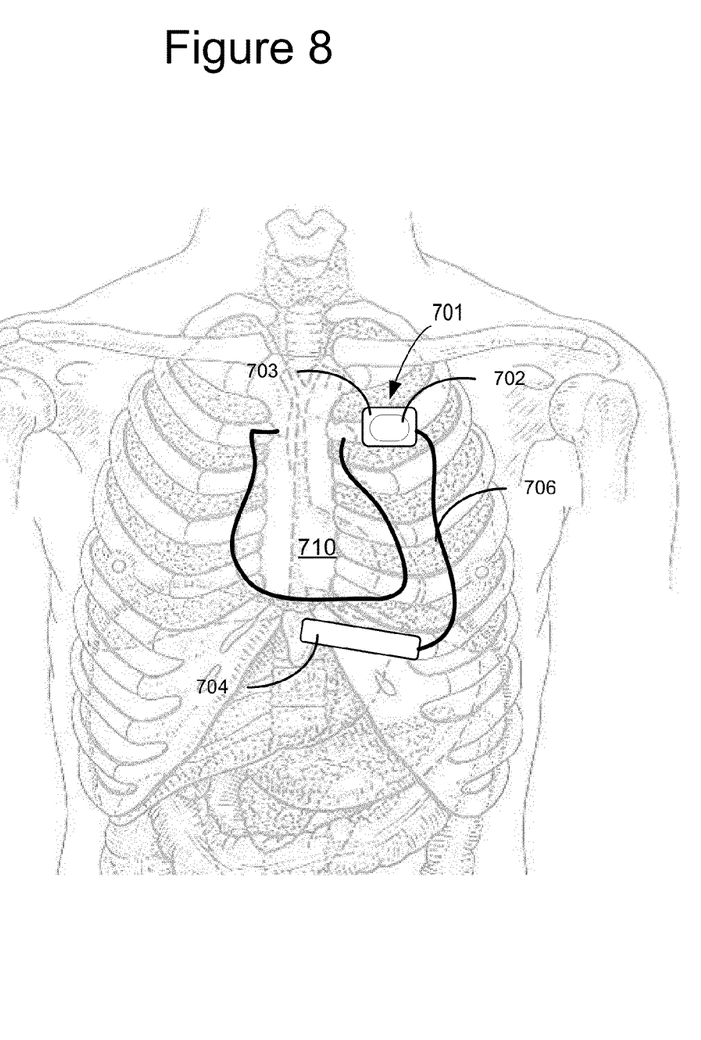
FIG. 8 shows another embodiment of an implantable medical device suitable for performing signal separation methodologies in accordance with the present invention.

Turning now to FIG. 8, the primary housing (e.g., the active or non-active can) of the PIMD 701, for example, may be configured for positioning outside of the rib cage at an intercostal or subcostal location, within the abdomen, or in the upper chest region (e.g., subclavian location, such as above the third rib). In one configuration, as is illustrated in FIG. 8, electrode subsystems of a PIMD system are arranged about a patient's heart 710. The PIMD system includes an electrode arrangement comprising a can electrode 702 provided on all or a portion of the PIMD housing 703. An optional electrode assembly 704 is also illustrated in FIG. 8 that may include one or more of electrodes, sensors, and multi-element electrodes. The optional electrode assembly 704 is coupled to the PIMD housing 703 using a lead 706.

In various configurations, the optional electrode subsystem 704 may include a combination of electrodes. The combination of electrodes of the optional electrode subsystem 704 may include coil electrodes, tip electrodes, ring electrodes, multi-element coils, spiral coils, spiral coils mounted on non-conductive backing, screen patch electrodes, and other electrode configurations. A suitable non-conductive backing material is silicone rubber, for example.

In one configuration, the lead assembly 706 is generally flexible and has a construction similar to conventional implantable, medical electrical leads (e.g., defibrillation leads or combined defibrillation/pacing leads). In another configuration, the lead assembly 706 is constructed to be somewhat flexible, yet has an elastic, spring, or mechanical memory that retains a desired configuration after being shaped or manipulated by a clinician. For example, the lead assembly 706 may incorporate a gooseneck or braid system that may be distorted under manual force to take on a desired shape. In this manner, the lead assembly 706 may be shape-fit to accommodate the unique anatomical configuration of a given patient, and generally retains a customized shape after implantation. Shaping of the lead assembly 706 according to this configuration may occur prior to, and during, PIMD implantation.

In accordance with a further configuration, the lead assembly 706 includes a rigid electrode support assembly, such as a rigid elongated structure that positionally stabilizes the electrode 704 with respect to the PIMD housing 703. In this configuration, the rigidity of the elongated structure maintains a desired spacing between the electrode 704 and PIMD housing 703, and a desired orientation of the electrode 704/housing 703 relative to the patient's heart. The elongated structure may be formed from a structural plastic, composite or metallic material, and includes, or is covered by, a biocompatible material. Appropriate electrical isolation between the PIMD housing 703 and electrode 704 is provided in cases where the elongated structure is formed from an electrically conductive material, such as metal.

In one configuration, the rigid electrode support assembly and the housing 703 define a unitary structure (e.g., a single housing/unit). The electronic components and electrode conductors/connectors are disposed within or on the unitary PIMD housing/electrode support assembly. At least two electrodes are supported on the unitary structure near opposing ends of the housing/electrode support assembly. The unitary structure may have an arcuate or angled shape, for example.

According to another configuration, the rigid electrode support assembly defines a physically separable unit relative to the housing 703. The rigid electrode support assembly includes mechanical and electrical couplings that facilitate mating engagement with corresponding mechanical and electrical couplings of the housing 703. For example, a header block arrangement may be configured to include both electrical and mechanical couplings that provide for mechanical and electrical connections between the rigid electrode support assembly and housing 703. The header block arrangement may be provided on the housing 703 or the rigid electrode support assembly. Alternatively, a mechanical/electrical coupler may be used to establish mechanical and electrical connections between the rigid electrode support assembly and housing 703. In such a configuration, a variety of different electrode support assemblies of varying shapes, sizes, and electrode configurations may be made available for physically and electrically connecting to a standard PIMD housing 703.

It is noted that the electrode(s) 704 and the lead assembly 706 may be configured to assume a variety of shapes. For example, the lead assembly 706 may have a wedge, chevron, flattened oval, or a ribbon shape, and the electrode 704 may include a number of spaced electrodes, such as an array or band of electrodes. Moreover, two or more electrodes 704 may be mounted to multiple electrode support assemblies 706 to achieve a desired spaced relationship amongst electrodes 704.

A PIMD of the present invention may be used within the structure of an advanced patient management (APM) medical system. Advanced patient management systems may allow physicians to remotely and automatically monitor cardiac and respiratory functions, as well as other patient conditions. In one example, implantable cardiac rhythm management systems, such as cardiac pacemakers, defibrillators, and resynchronization devices, may be equipped with various telecommunications and information technologies that enable real-time data collection, diagnosis, and treatment of the patient. Various embodiments described herein may be used in connection with advanced patient management. Methods, structures, and/or techniques described herein, which may be adapted to provide for remote patient/device monitoring, trending, diagnosis, therapy, or other APM related methodologies, may incorporate features of one or more of the following references: U.S. Pat. Nos. 6,221,011; 6,270,457; 6,277,072; 6,280,380; 6,312,378; 6,336,903; 6,358,203; 6,368,284; 6,398,728; and 6,440,066, which are hereby incorporated herein by reference.

Various embodiments described herein may be used in connection with heart failure monitoring, trending, diagnosis, and/or therapy. A PIMD of the present invention may incorporate features involving dual-chamber or bi-ventricular pacing/therapy, cardiac resynchronization therapy, cardiac function optimization, or other heart failure related methodologies. For example, a PIMD of the present invention may incorporate features of one or more of the following references: U.S. Pat. Nos. 6,411,848; 6,285,907; 4,928,688; 6,459,929; 5,334,222; 6,026,320; 6,371,922; 6,597,951; 6,424,865; 6,542,775; and 7,260,432, each of which is hereby incorporated herein by reference.

A PIMD may be used to implement various diagnostic functions, which may involve performing rate-based, pattern & rate-based, and/or morphological tachyarrhythmia discrimination analyses. Subcutaneous, cutaneous, and/or external sensors may be employed to acquire physiologic and non-physiologic information for purposes of enhancing tachyarrhythmia detection and termination. It is understood that configurations, features, and combination of features described in the present disclosure may be implemented in a wide range of implantable medical devices, and that such embodiments and features are not limited to the particular devices described herein.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A medical device, comprising:
a plurality of implantable electrodes configured for concurrent sensing of bio-impedance across multiple vectors to provide a plurality of impedance signals, the plurality of impedance signals comprising a primary impedance signal that includes a respiratory component and noise comprising a cardiac stroke component that corrupts the respiratory component; and
a processor coupled to the plurality of electrodes and configured to receive the plurality of impedance signals, the processor further configured to implement a signal separation technique on a combination of the plurality of impedance signals to separate a respiration signal from the plurality of impedance signals including the corrupting cardiac stroke component, the separated respiration signal characterized by the primary impedance signal substantially free of the corrupting cardiac stroke component.

2. The device of claim 1, further comprising communication circuitry coupled to the processor, the communication circuitry configured to transfer the separated respiration signal to a patient-external receiver.

3. The device of claim 1, wherein the processor is configured to form a linear combination of impedance signals that increases a signal-to-noise ratio for the separated respiration signal.

4. The device of claim 3, wherein the processor is configured to perform source separation when forming the linear combination of impedance signals.

5. The device of claim 1, wherein the processor is configured to perform adaptive noise cancellation to separate the respiration signal.

6. The device of claim 1, wherein:
the processor is configured to identify one or more additional separated signals with one or more signals of interest, the one or more signals of interest comprising a physiological signal; and
the physiological signal comprises a signal associated with one or more of respiration, cardiac activity, and a signal useful for detecting presence of thoracic fluid.

7. The device of claim 6, wherein the processor is configured to perform matching of a morphology of a separated signal with a morphology of a signal of interest.

8. The device of claim 6, wherein the processor is configured to perform matching of frequency content of a separated signal with frequency content of a signal of interest.

9. The device of claim 6, wherein the processor is configured to perform matching of timing of events within a separated signal with timing of events within a signal of interest.

* * * * *